(12) United States Patent
Iyunni

(10) Patent No.: US 11,633,579 B2
(45) Date of Patent: *Apr. 25, 2023

(54) DILATOR WITH SLIT AND SLIDABLE SLEEVE

(71) Applicant: Sainath Intellectual Properties, LLC, Pinellas Park, FL (US)

(72) Inventor: Venkata Sesha Sayi Nath Iyunni, Pinellas Park, FL (US)

(73) Assignee: SAINATH INTELLECTUAL PROPERTIES, LLC, Pinellas Park, FL (US)

( * ) Notice: Subject to any disclaimer, the term of this patent is extended or adjusted under 35 U.S.C. 154(b) by 871 days.

This patent is subject to a terminal disclaimer.

(21) Appl. No.: 16/574,661

(22) Filed: Sep. 18, 2019

(65) Prior Publication Data
US 2020/0009359 A1 Jan. 9, 2020

Related U.S. Application Data

(63) Continuation of application No. 15/508,709, filed on Mar. 3, 2017, now Pat. No. 10,493,250.

(51) Int. Cl.
| | |
|---|---|
| *A61M 25/00* | (2006.01) |
| *A61M 25/01* | (2006.01) |
| *A61M 25/09* | (2006.01) |
| *A61M 29/00* | (2006.01) |

(52) U.S. Cl.
CPC ........ *A61M 29/00* (2013.01); *A61M 25/0014* (2013.01); *A61M 25/0097* (2013.01); *A61M 25/01* (2013.01); *A61M 25/09041* (2013.01); *A61M 2025/0175* (2013.01); *A61M 2025/0188* (2013.01); *A61M 2205/0216* (2013.01)

(58) Field of Classification Search
CPC ... A61B 1/32; A61B 1/00073; A61B 1/00135; A61M 25/01; A61M 29/00; A61M 25/0662; A61M 25/0668; A61M 2025/0675; A61M 25/0015; A61M 2025/0188; A61M 2025/0175; A61M 25/0097; A61M 25/0014
See application file for complete search history.

(56) References Cited

U.S. PATENT DOCUMENTS

| | | | |
|---|---|---|---|
| 4,243,050 A | 1/1981 | Littleford | |
| 4,345,606 A | 8/1982 | Littleford | |
| 4,662,884 A * | 5/1987 | Stensaas | ........... A61F 2/04 606/152 |
| 4,726,369 A | 2/1988 | Mar | |
| 4,862,891 A | 9/1989 | Smith | |
| 5,048,508 A * | 9/1991 | Storz | ........... A61B 1/307 600/116 |
| 5,205,822 A | 4/1993 | Johnson | |

(Continued)

OTHER PUBLICATIONS

European Application No. 16867019.8, Extended European search report dated Jun. 18, 2019.

*Primary Examiner* — Bhisma Mehta
*Assistant Examiner* — William R Frehe
(74) *Attorney, Agent, or Firm* — Carlton Fields, PA; Eleanor Yost

(57) ABSTRACT

The invention includes a dilator comprising a tube and an elastic, unitary sleeve that is slidable both longitudinally and transversely to the cylindrical barrel when disposed on the tube.

8 Claims, 4 Drawing Sheets

(56) References Cited

U.S. PATENT DOCUMENTS

| | | | |
|---|---|---|---|
| 5,380,290 A * | 1/1995 | Makower | A61M 25/0662 604/164.01 |
| 5,405,334 A | 4/1995 | Roth | |
| 5,460,185 A * | 10/1995 | Johnson | A61M 25/013 600/585 |
| 5,718,693 A * | 2/1998 | Gupta | A61B 17/3415 604/171 |
| 6,143,016 A * | 11/2000 | Bleam | A61F 2/958 606/198 |
| 6,152,944 A * | 11/2000 | Holman | A61M 25/104 606/198 |
| 6,277,094 B1 * | 8/2001 | Schendel | A61B 17/3439 604/104 |
| 6,582,401 B1 * | 6/2003 | Windheuser | A61M 25/00 604/523 |
| 6,583,401 B2 | 6/2003 | Windheuser | |
| 6,764,464 B2 | 7/2004 | McGuckin, Jr. et al. | |
| 7,002,098 B2 * | 2/2006 | Adams | A61M 5/3286 219/121.64 |
| 7,744,571 B2 | 6/2010 | Fisher et al. | |
| 7,892,201 B1 * | 2/2011 | Laguna | A61M 25/1034 604/96.01 |
| 10,493,250 B2 * | 12/2019 | Iyunni | A61M 25/00 |
| 2004/0064147 A1 | 4/2004 | Struble | |
| 2004/0087984 A1 * | 5/2004 | Kupiecki | A61B 17/11 606/153 |
| 2004/0093005 A1 * | 5/2004 | Durcan | A61M 25/10 606/194 |
| 2005/0197663 A1 * | 9/2005 | Soma | A61M 25/09041 606/108 |
| 2006/0004439 A1 * | 1/2006 | Spenser | A61F 2/2436 623/2.11 |
| 2007/0250001 A1 * | 10/2007 | Hilaire | A61F 2/954 604/103.04 |
| 2009/0018508 A1 * | 1/2009 | Fisher | A61M 25/0668 604/167.04 |
| 2009/0182363 A1 | 7/2009 | Shamay | |
| 2010/0262218 A1 | 10/2010 | Deshmukh | |
| 2010/0286565 A1 * | 11/2010 | Nanto | G06Q 20/20 600/585 |
| 2014/0171913 A1 * | 6/2014 | Watanabe | A61M 25/0026 604/528 |
| 2014/0276436 A1 * | 9/2014 | Lafitte | A61M 25/0662 604/164.13 |
| 2014/0277022 A1 * | 9/2014 | Perrin | A61B 17/3209 606/167 |
| 2015/0005479 A1 * | 1/2015 | Choi | C07K 14/21 204/660 |
| 2015/0331191 A1 * | 11/2015 | Hasegawa | G02B 6/44 385/38 |

* cited by examiner

DILATOR WITH SLIT AND SLIDABLE SLEEVE

CROSS-REFERENCE TO RELATED APPLICATIONS

This application is a continuation of U.S. Ser. No. 15/508,709, which claims priority to International Application No. PCT/US2016/062234, 1, which claims priority to U.S. provisional application entitled DILATOR WITH SLIT AND SLIDABLE SLEEVE, Appl. No. 62/257,509, which was filed Nov. 19, 2015, the disclosure and entire contents of which are each hereby incorporated by reference in their entireties.

FIELD OF THE INVENTION

The field relates to dilators used in surgical procedures to introduce catheters into the body of patients.

BACKGROUND

Dilators with tubes that are solid are known. Tear away dilators are known that allow a wire to be torn through the wall of the dilator. None of these known devices provide the advantages of a dilator with a slidable sleeve.

SUMMARY

A dilator or cannula comprises a tube with a silt, the slit being arranged longitudinally along the length of a side of the tube, such that the tube is removable from the guidewire by pulling the guidewire through the slit, and a slidable sleeve, arranged on an outer circumference of the tube, such that the slidable sleeve closes the slit of the tube during dilation, while allowing the tube to be inserted along the guidewire by sliding the tube through the sleeve.

A method of using the dilator or cannula, described above, comprises inserting a guidewire into a lumen or cavity in a patient, placing the tube of the dilator onto the guidewire, using the slit in the tube to fit the tube of the dilator over and around the guidewire, sliding the slidable sleeve over the tube, and holding the slidable sleeve with a hand, while sliding the tube through the slidable sleeve, along the guidewire and into the lumen or cavity of the patient.

In one example, the slidable sleeve is made of a transparent or translucent material. The slidable sleeve may be made of an elastic material, such that the slidable sleeve applies a force on the tube, tending to close the slit of the tube, when the slidable sleeve is disposed around the outer circumference of the tube. In one example, the tube has a tip. A tip of the tube of the dilator may be shaped to dilate tissue, such as a cone-shaped tip or a funnel-shaped tip.

In one example, a dilator comprises: a guide; a tube comprising a first end, a second end, and a wall extending between the first end and the second end, wherein the wall comprises a cylindrical barrel and a tapered tip, wherein the first end comprises a first opening and the second end comprises a second opening, and the guide extends through the first opening, the cylindrical barrel, the tapered tip and the second opening, and the cylindrical barrel and the tapered tip comprise a solid wall and a slit extending through the solid wall longitudinally from the first opening to the second opening, opposite of the first opening. For example, the sleeve may be a transparent or translucent sleeve, which allows a surgeon to view that the slit remains closed, while the surgeon inserts the tube along the guide through tissues of a patient through which the guide has been inserted, such as by a large needle or trochar. In one example, the sleeve is an elastic material, and the elastic material applies a bias force to the tube of the dilator, when the sleeve is disposed onto the outer wall of the tube. Alternatively, or in addition to the elastic bias force, a surgeon may hold the sleeve during dilation, such that the sleeve applies a force closing the slit of the tube. Either way, the slit of the tube is closed during insertion of the dilator along the guide. When withdrawn, the tube may be easily removed from the guide by releasing the sleeve and/or removing the sleeve from the tube, and slipping the tube off of the guide by directing the guide through the slit in the wall of the tube, which slit is open when the sleeve is removed from the tube.

In another example, the dilator further comprises a side opening, and the side opening is provided in a side wall of the tube, such that the guide exits through the side opening.

In one example, the guide is a wire. A sleeve may be comprised of a fluoropolymer, such as a tetrafluoroethylene polymer or co-polymer. In one example, the sleeve is an elastic material, such as an elastomer, elastomeric copolymer, spring steel or spring nickel alloy. A spring metal or a polymer may be sufficiently elastic to keep the slit of the tube closed, while advancing the tube along the guide. In one example, the dilator may comprise a tapered tip, wherein the tapered tip extends from the cylindrical barrel of the tube to the second end of the tube. The slit may extend through a solid wall of the tip, such that the slit extends, uninterrupted, from the first end to the second end of the tube. The opening at the second end is sized to allow the guide to pass through the opening at the second end, even if the end is a tapered tip.

A method of using the dilator comprises inserting the guide into a cavity, placing the dilator onto the guide, holding the sleeve disposed on the tube, such that the slit in the tube is closed by the sleeve, and advancing the tube along the guide into the cavity by sliding the tube through the sleeve, while holding the sleeve.

If the tube comprises a side opening with the guide passing through the side opening, then a second dilator may be introduced through the side opening of a first dilator, replacing the first dilator, as the first dilator is peeled away from the second dilator. For example, the slidable sleeve may be disposed at an end of the tube distal from the end of the tip introduced into the vessel, such that the slit opens as the second tube is inserted into the side opening and along the channel defined by the wall of the first tube.

BRIEF DESCRIPTION OF THE DRAWINGS

The following drawings are illustrative examples and do not further limit any claims that may eventually issue.

When the same reference characters are used, these labels refer to similar parts in the examples illustrated in the drawings.

DETAILED DESCRIPTION

Figure 1:
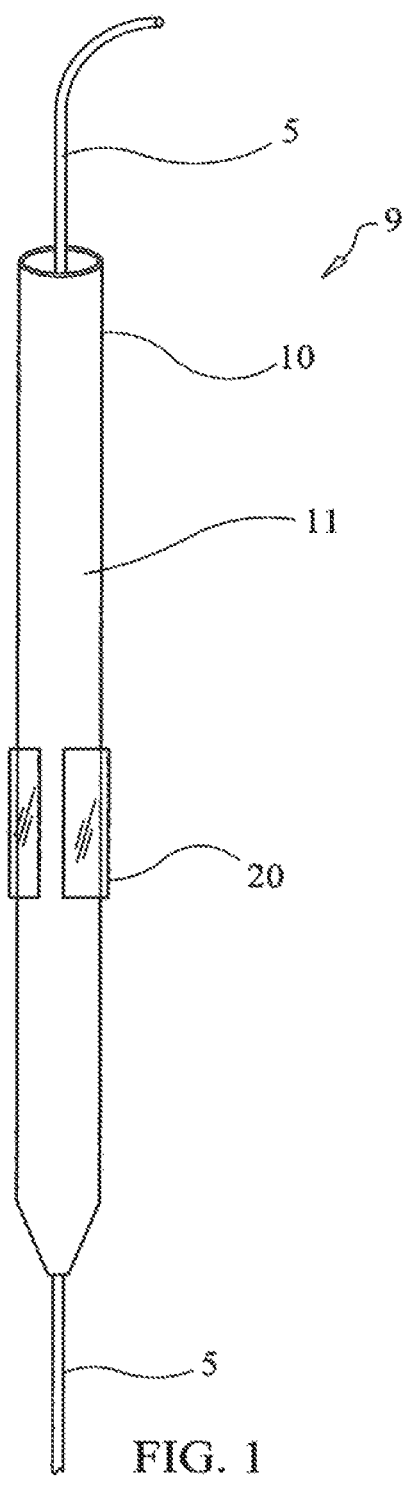
FIG. 1 illustrates an example of a dilator.

As illustrated in FIG. 1, an example of a dilator 9 comprises a tube 10 with a slit 12, the slit 12 being closed when pressure is applied by or to a slip sleeve 20. In one example, the slip sleeve 20 is made of a transparent material that is elastic, such that a sufficient bias force is applied by the sleeve 20 on the tube 10 to close the slit 12 of the tube 10, when the sleeve 20 is fit over the tube 10. A guide 5 extends through the center of the tube 10 and through the tip 14 of the tube 10 of the dilator 9. The tube 10 comprises a cylindrical barrel 11 and a tip 14 having an opening 16. A guide 5 extends through the tube 10 and an inner diameter of the opening 16 is sized to accommodate the guide 5, which may be a wire or the like.

In one example, the slip sleeve 20 is a partial circular cylinder with an opening 22. The opening 22 may be sized with the sleeve material to provide an inner diameter smaller than the outer diameter of the tube 10. The slip sleeve 20 may be fit onto the tube 10 by stretching, elastically the opening 22, and the elasticity can apply a bias force on the tube 10, at least partially serving to close the slit 12 of the tube, when the sleeve 20 is slipped onto the tube 10.

When put into use, the dilator 10 may be placed on the guide 5 prior to being used to dilate an incision or puncture through which the guide 5 extends. The slip sleeve 20, when placed on the tube 10 may apply a bias force to the tube, tending to close the slit 12 in the wall of the barrel 11 and tip 14 of the tube 10. A surgeon may apply additional force to the sleeve 20 by holding the sleeve 20 during insertion of the tube 10 of the dilator along the guide 5 into the tissue of a patient, dilating the incision or puncture or both through which the guide 5 passes. With one hand, a surgeon may advance the tube 10, while the other hand holds the slip sleeve 20. The tube and sleeve 20 may be made of materials that allow the tube 10 to slip through the sleeve 20 while both are held by the surgeon. Therefore, the tube 10 may be advanced along the guide 5 by sliding the tube 10 through the slip sleeve 20, while the slip sleeve 20 keeps the slit 12 closed.

When the tissue of the patient is dilated by insertion of the tube 10 along the guide 5, the tube acts as a dilator. The dilator may be allowed to remain for a time to allow the dilation to successfully open a path along the guide 5. Another tube may be asserted within or outside of the tube 10 to further dilate the path along the guide 5 in the tissue of the patient. Alternatively, a surgical instrument may be inserted along the guide, after the tissues of the patient are dilated.

The tube 10 may be withdrawn from the patient and may be quickly removed from the guide by removing the slip sleeve 20 and removing the guide 5 from the tube 10 through the slit 12, without having to slide the tube along the guide 5 to the free end of the guide 5. Also, the slit is already open and the slit need not be torn, cut or the wire used to split the tube 10 along a weakened tear line, as in some devices. This tearing and pulling required of prior art dilators leads to movement of the guide 5 and applies forces that can cause unintended damage to the tissues of the patient or displacement of the guide 5 from its intended location in the patient. Therefore, the ability of the slit 12 to be opened or closed by the slidable sleeve 20 provides a significant advantage over known dilators.

Figure 2:
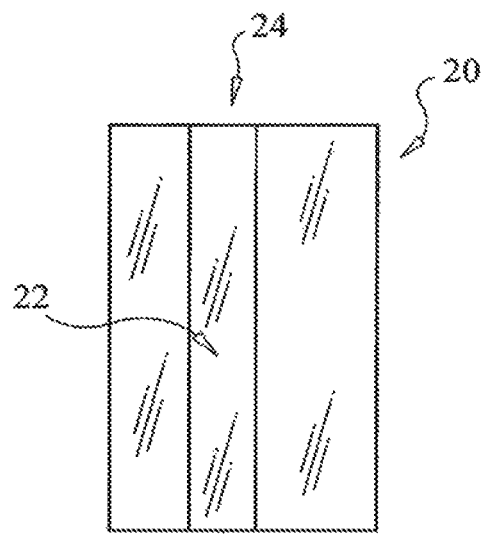
FIG. 2 illustrates a side view of a slidable sleeve.
Figure 3:
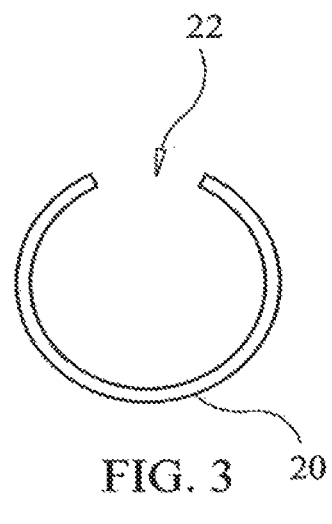
FIG. 3 illustrates an end view of the slidable sleeve in FIG. 2.
Figure 4:
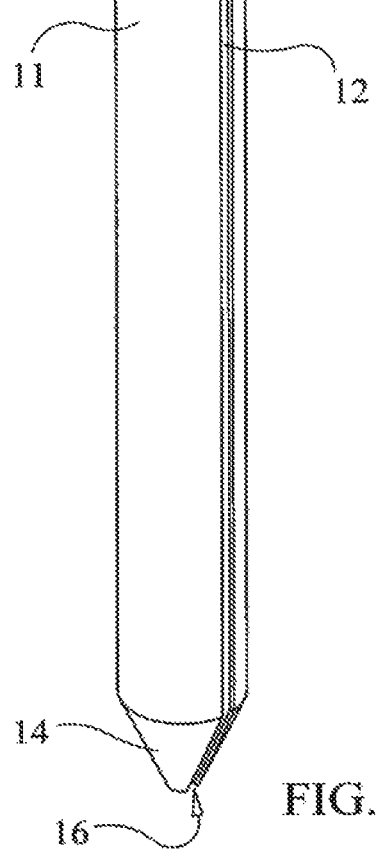
FIG. 4 illustrates a perspective view of an example of a tube of the dilator of FIG. 1.
Figure 5:
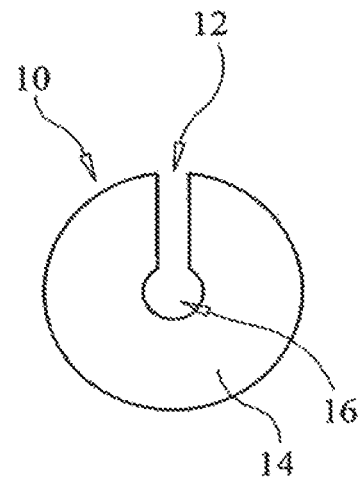
FIG. 5 illustrates an end view, showing the tip of the tube illustrated in FIG. 4.
Figure 6:
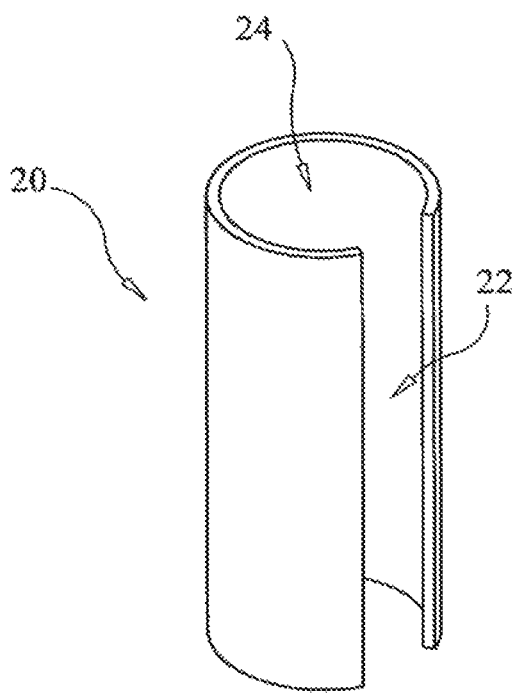
FIG. 6 illustrates a perspective view of another example of a slidable sleeve.

FIG. 2 illustrates a transparent slip sleeve 20 with a slit 22. FIG. 3 illustrates another view of a slip sleeve 20 with a slit 22 and showing the channel 24 formed by the outer wall of the slip sleeve 20. FIG. 4 illustrates the slit 12 in a dilator 10. An opening 16 in the tip 14 is provided for the guidewire 5 to pass through. Another, longer and non-transparent slip sleeve is shown in FIG. 6. FIG. 5 illustrates a detailed view of the opening 16 in the tip 14. The channel 24 may be sized to fit over the outer diameter of the dilator 10 shaft 11 illustrated in FIG. 4.

Figure 7:
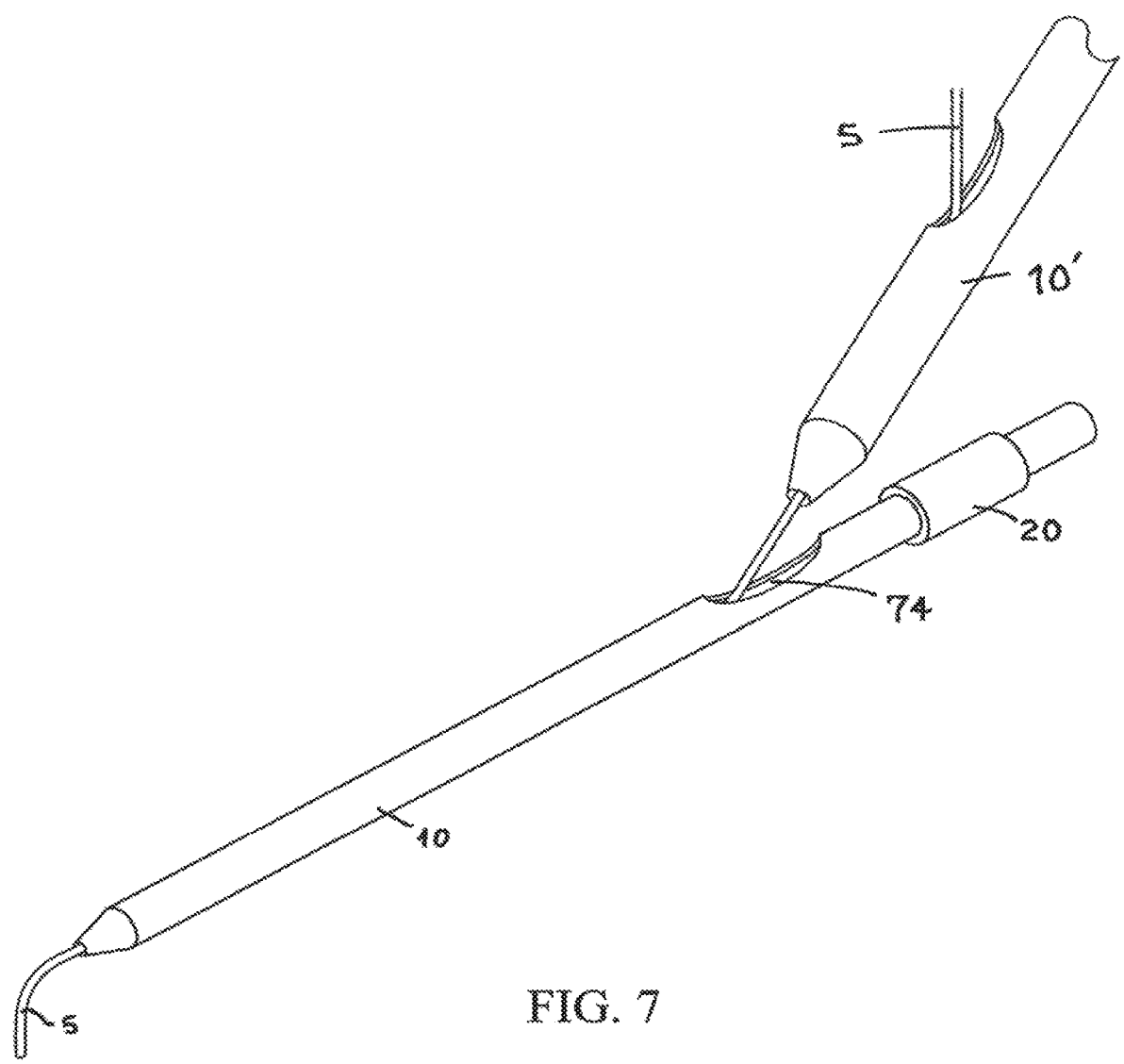
FIG. 7 illustrates another example of a dilator with a slidable sleeve.

In the example of FIG. 7, a guidewire 5 extends through a first dilator 10, exiting out of a hole 74 formed in the side of the dilator 10. A second dilator 10' has a larger outer diameter and is closed around the guidewire 5, which likewise exits from a hole formed in the side of the dilator. As the second dilator 10' is advanced along the guidewire 5, it enters the hole 74 formed in the side of the first dilator 10. The slip sleeve is disposed at a location distal from the tip of the first dilator 10, such that second dilator 10' can cause the slit in the first dilator 10 to open as the second dilator 10' is inserted into the hole 74 of the first dilator 10. Thus, the second dilator 10' may be inserted into the first dilator 10, even though the second dilator 10' has a greater diameter than the first dilator 10. As the second dilator 10' is advanced, the first dilator 10 may be peeled away and removed from the guidewire 5 quite easily, allowing the second dilator 10' to replace the first dilator 10. In this way, successive dilators of greater diameter may be inserted into a lumen in the body, expanding the lumen, gradually, without damaging the lumen, until a medical device can be fit through the dilator and into the lumen.

The slit 12 provides an advantage over prior art devices, because the preexisting slit 12 easily opens when the slip sleeve 20 is held in a way that does not prevent the slit 12 from opening. In one example, the slip sleeve 20 may be removed from the dilator when the dilator is being removed from the guidewire. In another example, the slip sleeve may be moved to a distal end of a dilator, when the guidewire is being removed from the dilator. In yet another example, the slit 22 in the slip sleeve 20 may be aligned with the slit 12 in the shaft 11 of the dilator 10, when the guidewire 5 is being removed from the dilator 10. In each example, removing the guidewire does not require peeling of the dilator from the wire, which can be difficult. Also, the second dilator 10' need not be threaded onto the guidewire 5, which can be tedious and time consuming, especially since the free end of a guidewire 5 may extend a significant distance. Thus, the advantages of the features illustrated in the drawings reduce the time that it takes to introduce one or more dilators into a lumen in order to introduce a medical device into the lumen.

Figure 8:
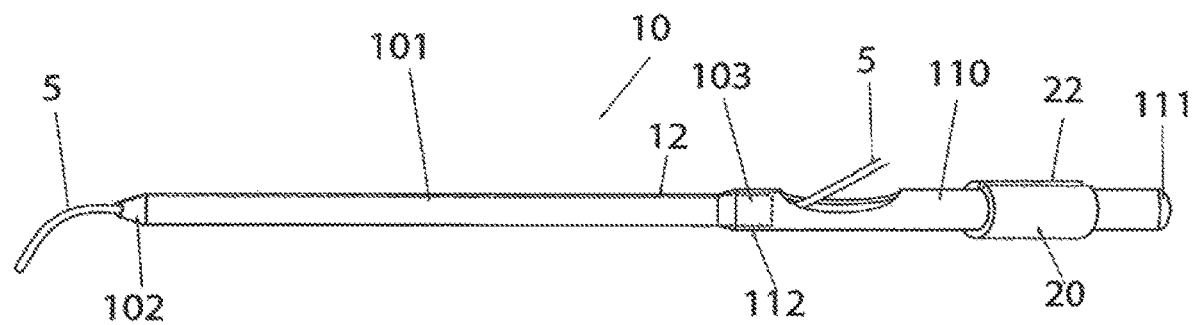
FIG. 8 illustrates another example of a dilator.

FIG. 8 shows an example of a dilator 10 comprising a tube 101 having a first end 103, a second end 102, and a wall extending between the first end and the second end, wherein the wall comprises a cylindrical barrel, wherein the first end 103 comprises a first opening and the second end 102 comprises a second opening, a channel extending the length of the barrel from the first opening, through the cylindrical barrel and to the second opening, and the cylindrical barrel comprises a solid wall and a slit 12 extending entirely through the solid wall, longitudinally, from the first opening to the second opening, opposite of the first opening. In this example, an end cap 110 comprises an open end 112 and a closed end 111, having an inner diameter at the open end, the inner diameter sized to matingly fit over an outer diameter of the first end 103 of the tube 101, and the closed end 111 is opposite of the open end 112. The end cap 110 may have an outer wall defining a cavity. For example, an opening in the wall may be provided such that access to the cavity is made for introduction of another dilator into the cavity. The opening may be disposed between the open end 112 and the closed end 111, and the opening may have a length less than the length of the end cap and a width less than the length of the opening. The length of the opening may be larger than the width of the opening to facilitate introduction of another dilator into the cavity. A slit 12 may be provided that extends entirely through the thickness of the outer wall of the end cap. For example, the slit extends from the opening to the open end 112 of the end cap 110, wherein by aligning the slits, the open end 112 of the end cap 110 is joined to the first end 103 of the tube 101 such that the slit 12 in the end cap aligns with the slit 12 of the tube. Thus, the slit 12 of the end cap and the slit 12 of the tube define a continuous slit 12 from the opening of the end cap 110 to the second opening of the tube distal from the end cap 110, for example. In one example, a sleeve 20 may be disposed on the tube or the end cap. The sleeve 20 may have a sleeve length less titan the length of the end cap. A sleeve slit 22 may extend through a wall thickness of the sleeve 20 along the sleeve length. For example, a flexibility and an inner diameter of the sleeve may be selected such that the tube and the end cap slidably extend through the sleeve. In one example, the tube may comprise, in addition to the cylindrical barrel 101, a tapered tip 102, wherein the tapered tip 102 extends from the cylindrical barrel 101 to an end of the barrel 101, and the slit 12 of the dilator 10 extends through the solid wall of the tip 102, such that the slit 12 extends, uninterrupted, the length of the barrel 101 of the tube and to opening in the end cap 110. In one example, the opening at the second end is a hole sized to allow the guidewire to pass through the hole. For example, the hole may have a diameter, when the slit through the tapered tip is closed, that is selected to equal an outer diameter of the guidewire. In one example, the slit may be closed by elasticity or elastic memory of the sleeve. Alternatively, a user may pinch the sleeve slightly to close the slit 12, applying a compressive stress to the barrel 101 via the sleeve 20.

In one example, a method of making the dilator comprises extruding the tube and molding the end cap. The tube and end cap are then joined together, such as by fusing, welding or adhering the end cap to the tube. The end cap may be molded such that the end cap has an inner diameter at the open end of the end cap that is sized to matingly fit over an outer diameter of the tube. The step of joining the end cap to a proximal end of the tube may follow a step of aligning of the respective slits, such that a continuous slit is formed. The open end of the end cap may be joined to the proximal end of tube while aligning the slit in the end cap with the slit in the tube, forming a slit extending the entire distance from the opening in the side wall of the end cap to a distal end of the tube, opposite of the proximal end of the tube. In one example, a plurality of sleeves 20 may be provided. One of the plurality of sleeves may be disposed on the barrel 101 while another of the plurality of sleeves may be disposed on the end cap 110. The slit 22 of the sleeve 20 on the end cap may be rotated away from the slit 12 of the dilator 10, such that the sleeve 20 may be used to push against the guide 5 to force the guide 5 through the slit 12, by advancing the sleeve 20 forward, toward the tip 102, for example.

This detailed description provides examples including features and elements of the claims for the purpose of enabling a person having ordinary skill in the art to make and use the inventions recited in the claims. However, these examples are not intended to limit the scope of the claims, directly. Instead, the examples provide features and elements of the claims that, having been disclosed in these descriptions, claims and drawings, may be altered and combined in ways that are known in the art.

I claim:

1. A dilator comprising:
a tube having a first end, a second end, and a tube wall extending between the first end and the second end, wherein the tube wall comprises a cylindrical barrel and a tube wall longitudinal length, wherein the first end comprises a first end opening and the second end comprises a second end opening,
a channel extending a length of the cylindrical barrel from the first end opening, through the cylindrical barrel, and to the second end opening,
wherein the cylindrical barrel comprises a solid wall having a constant outer diameter and a tube slit extending entirely through the solid wall, longitudinally, from the first end opening to the second end opening, opposite of the first end opening;
an elastic, unitary sleeve, slidable longitudinally and transversely to the cylindrical barrel when disposed on the tube, comprising
at least one sleeve opening,
a sleeve wall having a sleeve wall longitudinal length that is less than the tube wall longitudinal length,
a sleeve slit extending longitudinally entirely through a wall thickness of the sleeve wall, wherein the sleeve slit is selectively mis-alignable with the tube slit to prevent removal of the dilator from a guide, an inner diameter of the sleeve wall forming a sleeve channel, and wherein the elastic, unitary sleeve is removably disposed on the tube by inserting the tube inside the sleeve channel thereby elastically stretching the elastic, unitary sleeve; and
wherein the tube slit is closed by the elastic, unitary sleeve during dilation.

2. The dilator of claim 1, further comprising wherein the guide is a guidewire.

3. The dilator of claim 1, wherein the elastic, unitary sleeve is comprised of a fluoropolymer.

4. The dilator of claim 3, wherein the elastic, unitary sleeve is comprised of a tetrafluoroethylene polymer or co-polymer.

5. The dilator of claim 1, wherein the elastic, unitary sleeve is comprised of an elastomer.

6. The dilator of claim 1, wherein the second end further comprises a tapered tip.

7. A method of using the dilator of claim 1, comprising:
inserting the guide into a patient cavity;
placing the dilator onto the guide by aligning the sleeve slit and the tube slit and passing the guide through the sleeve slit and the tube slit;
holding the elastic, unitary sleeve disposed on the tube, such that the tube slit is closed by compression of the elastic, unitary sleeve; and
advancing the dilator along the guide into the patient cavity by sliding the tube and the elastic, unitary sleeve, while holding the elastic, unitary sleeve.

8. A method of using the dilator of claim 1, comprising:
inserting the guide into a patient cavity;
placing the dilator onto the guide by aligning the sleeve slit and the tube slit and passing the guide through the sleeve slit and the tube slit;
rotating the elastic, unitary sleeve disposed on the tube transversely until the sleeve slit is misaligned with the tube slit thereby preventing the guide from passing through the sleeve slit and the tube slit;

advancing, the dilator along the guide into the patient cavity by sliding the tube and the elastic, unitary sleeve, while holding the elastic, unitary sleeve.

\* \* \* \* \*